US007946977B2

(12) United States Patent
Klearman et al.

(10) Patent No.: US 7,946,977 B2
(45) Date of Patent: May 24, 2011

(54) PHALLIC DEVICES WITH AUDIO FEATURES AND RELATED METHODS

(75) Inventors: Jeffrey D Klearman, St. Louis, MO (US); Cheryl J Berry, St. Louis, MO (US)

(73) Assignee: My Little Secret, LLC, St. Louis, MO (US)

( * ) Notice: Subject to any disclaimer, the term of this patent is extended or adjusted under 35 U.S.C. 154(b) by 1074 days.

(21) Appl. No.: 11/081,050

(22) Filed: Mar. 15, 2005

(65) Prior Publication Data

US 2006/0084837 A1 Apr. 20, 2006

Related U.S. Application Data

(60) Provisional application No. 60/607,309, filed on Sep. 7, 2004, provisional application No. 60/610,616, filed on Sep. 16, 2004.

(51) Int. Cl.
*A61F 5/00* (2006.01)

(52) U.S. Cl. ............................................ 600/38; 601/46

(58) Field of Classification Search .................... 600/38; 601/46–47

See application file for complete search history.

(56) References Cited

U.S. PATENT DOCUMENTS

| | | | | |
|---|---|---|---|---|
| 1,703,642 | A | 2/1929 | Sticht | |
| 3,669,100 | A | 6/1972 | Csanad | |
| 4,055,170 | A | 10/1977 | Nohmura | |
| 4,296,376 | A | 10/1981 | Bartol, Jr. | |
| 4,593,376 | A * | 6/1986 | Volk | 705/16 |
| 4,722,326 | A | 2/1988 | Ruderian | |
| 4,722,327 | A | 2/1988 | Harvey | |
| 5,067,480 | A | 11/1991 | Woog et al. | |
| 5,076,261 | A | 12/1991 | Black | |
| 5,163,447 | A | 11/1992 | Lyons | |
| 5,165,131 | A | 11/1992 | Staar | |
| 5,283,970 | A | 2/1994 | Aigner | |
| 5,345,700 | A * | 9/1994 | Norment | 36/139 |
| 5,377,692 | A | 1/1995 | Pfeil | |
| 5,425,078 | A | 6/1995 | Stern | |
| 5,438,726 | A | 8/1995 | Leite | |
| 5,460,597 | A | 10/1995 | Hopper | |
| RE35,082 | E | 11/1995 | Kuo | |
| 5,468,172 | A | 11/1995 | Basile | |
| 5,490,206 | A | 2/1996 | Stern | |
| 5,504,836 | A | 4/1996 | Loudermilk | |
| 5,524,638 | A | 6/1996 | Lyons | |

(Continued)

FOREIGN PATENT DOCUMENTS

DE 4306670 9/1994

(Continued)

OTHER PUBLICATIONS http://www.voice-express.com/news/, Products that Deliver Your Message, accessed Sep. 7, 2005, 8 pages.

*Primary Examiner* — John P Lacyk
(74) *Attorney, Agent, or Firm* — Lathrop & Gage LLP

(57) ABSTRACT

A phallic device for sexual stimulation generally includes a housing and at least one end cap attached to the housing. The end cap includes a data access device for accessing audio data from a data device. The end cap further includes a sound emitter for emitting audio corresponding to the audio data accessed by the data access device from the data device.

5 Claims, 10 Drawing Sheets

U.S. PATENT DOCUMENTS

| | | | | |
|---|---|---|---|---|
| 5,570,414 | A | 10/1996 | Stern | |
| 5,573,499 | A | 11/1996 | McAllister | |
| 5,690,603 | A | 11/1997 | Kain | |
| 5,769,090 | A | 6/1998 | Brown | |
| 5,782,779 | A | 7/1998 | Kilgore | |
| 5,928,170 | A | 7/1999 | Garrigan | |
| 5,956,682 | A | 9/1999 | Loudermilk et al. | |
| 6,028,531 | A | 2/2000 | Wanderlich | |
| 6,110,102 | A | 8/2000 | Harrison | |
| 6,185,851 | B1 | 2/2001 | Loudermilk et al. | |
| 6,263,310 | B1 | 7/2001 | Loudermilk et al. | |
| 6,356,626 | B1 | 3/2002 | Ohara et al. | |
| 6,377,926 | B2 | 4/2002 | Loudermilk | |
| 6,381,573 | B1 | 4/2002 | Loudermilk et al. | |
| 6,393,401 | B1 | 5/2002 | Loudermilk et al. | |
| 6,393,402 | B1 | 5/2002 | Loudermilk et al. | |
| 6,529,873 | B1 * | 3/2003 | Owen | 704/260 |
| 6,592,516 | B2 | 7/2003 | Lee | |
| 2001/0014623 | A1 * | 8/2001 | Kawai et al. | 463/44 |
| 2002/0065477 | A1 | 5/2002 | Boyd et al. | |
| 2002/0133102 | A1 | 9/2002 | Quan | |
| 2003/0204236 | A1 | 10/2003 | Letort | |
| 2004/0034495 | A1 * | 2/2004 | Marlett | 702/117 |
| 2004/0082831 | A1 | 4/2004 | Kobashikawa et al. | |
| 2004/0097852 | A1 | 5/2004 | Boyd et al. | |
| 2004/0125120 | A1 | 7/2004 | Weiner | |

FOREIGN PATENT DOCUMENTS

| | | |
|---|---|---|
| DE | 10038271 | 2/2002 |

* cited by examiner

PHALLIC DEVICES WITH AUDIO FEATURES AND RELATED METHODS

CROSS-REFERENCE TO RELATED APPLICATIONS

This application claims the benefit of U.S. Provisional Application No. 60/607,309, filed on Sep. 7, 2004. This application also claims the benefit of U.S. Provisional Application No. 60/610,616, filed on Sep. 16, 2004. The disclosures of the above applications are incorporated herein by reference.

FIELD

The present invention generally relates to phallic devices for sexual stimulation that also include audio features for playing prerecorded audio and/or personalized audio.

BACKGROUND

Dildos and vibrators are distributed throughout the world generally in sexual novelty shops and through internet merchants. These devices can be used as sexual aids and given merely as gag gifts, for example, at an office party to embarrass the recipient. Dildos and vibrators are usually phallic shaped so as to resemble the form (if not the size) of the penis or phallus. Typically, the term "dildo" generally refers to and includes phallic-shaped devices that are static or non-vibrating, while the term "vibrator" generally refers to and includes phallic-shaped devices that include a system for causing vibration of the device.

SUMMARY

According to one aspect of the present invention, a phallic device for sexual stimulation generally includes a housing and at least one end cap attached to the housing. The end cap includes a data access device for accessing audio data from a data device. The end cap further includes a sound emitter for emitting audio corresponding to the audio data accessed by the data access device from the data device.

Further aspects and features of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Corresponding reference numerals indicate corresponding features throughout the several views of the drawings.

DETAILED DESCRIPTION OF EXEMPLARY EMBODIMENTS

The following description of exemplary embodiments is merely exemplary in nature and is in no way intended to limit the invention, its applications, or uses.

A phallic device according to one aspect of the present invention generally includes a housing and at least one end cap attached to the housing. The end cap includes a data access device or means for accessing audio data from a data device. The end cap also includes a sound emitter or means for emitting audio. During operation, the sound emitter produces audio (e.g., voice messages, music, instructions, natural sounds, artificial sounds, etc.) corresponding to the audio data accessed by the data access device. In some embodiments, the end cap is configured to resemble a figurine of a famous person, and the audio data includes voice messages with at least one predetermined speech characteristic (e.g., inflections, accents, a foreign language, etc.) coordinated or associated with the famous person.

Another aspect of the present invention provides an end cap for a phallic device. In one embodiment, the end cap is configured to be retrofit (e.g., threadably engaged, etc.) onto an existing phallic device to thereby provide the phallic device with audio capabilities. For example, an existing end cap of the phallic device can be removed and replaced with an end cap having a data access device and a sound emitter.

In another aspect of the invention, the invention provides a plurality of interchangeable data devices each having audio data. By selecting from amongst the interchangeable data devices, the user can thus select the audio that is played by the phallic device.

In yet another aspect, the invention provides a plurality of interchangeable end caps. Each end cap includes a data device having audio data, and a data access device or means for accessing the audio data. Each end cap also includes a sound emitter or means for emitting audio that corresponds to the audio data. Accordingly, the user can thus select which audio is played by selecting an end cap and then attaching the selected end cap to the phallic device.

Further aspects include methods of using such phallic devices, end caps, and audio features thereof. For example, various methods include customizing the audio data for playback by the phallic device as described herein.

Figure 1:
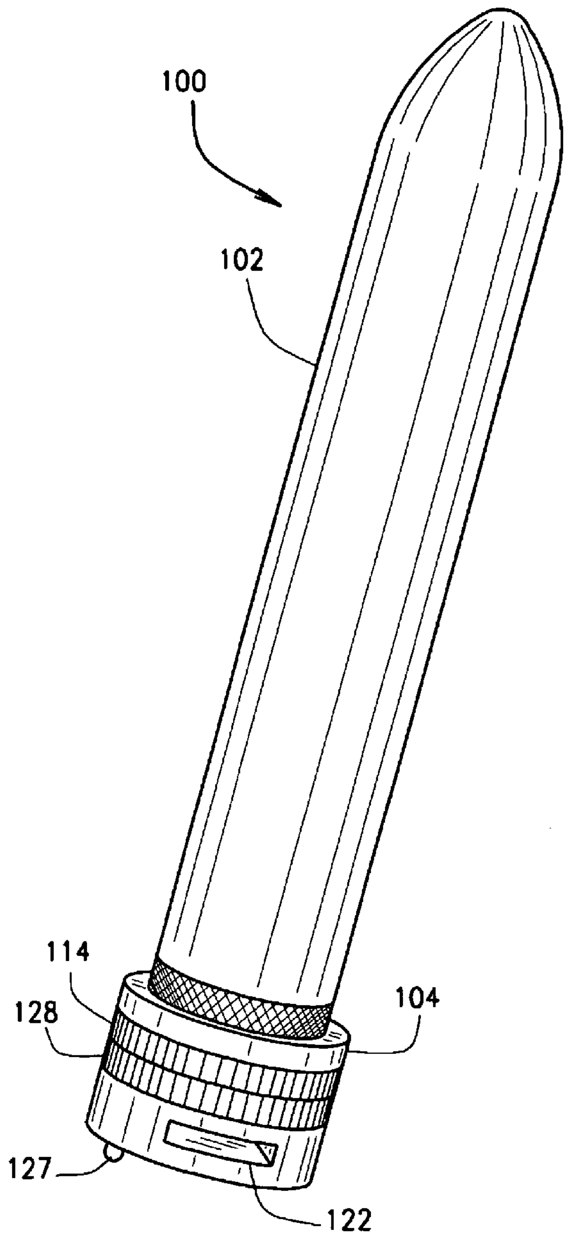
FIG. 1 is a perspective view of a phallic device including an end cap having an audio system according to one embodiment of the present invention.
Figure 2:
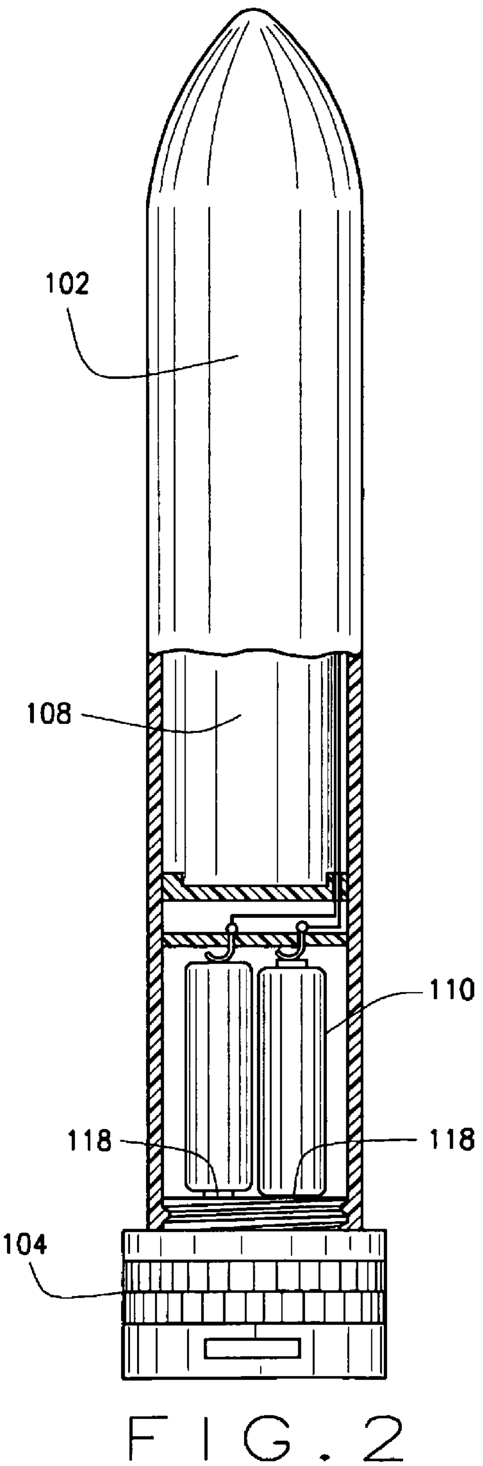
FIG. 2 is a perspective view of the phallic device shown in FIG. 1 with a portion of the housing removed to illustrate the batteries, vibration-generating motor, and threaded engagement between the end cap and the housing.
Figure 3:
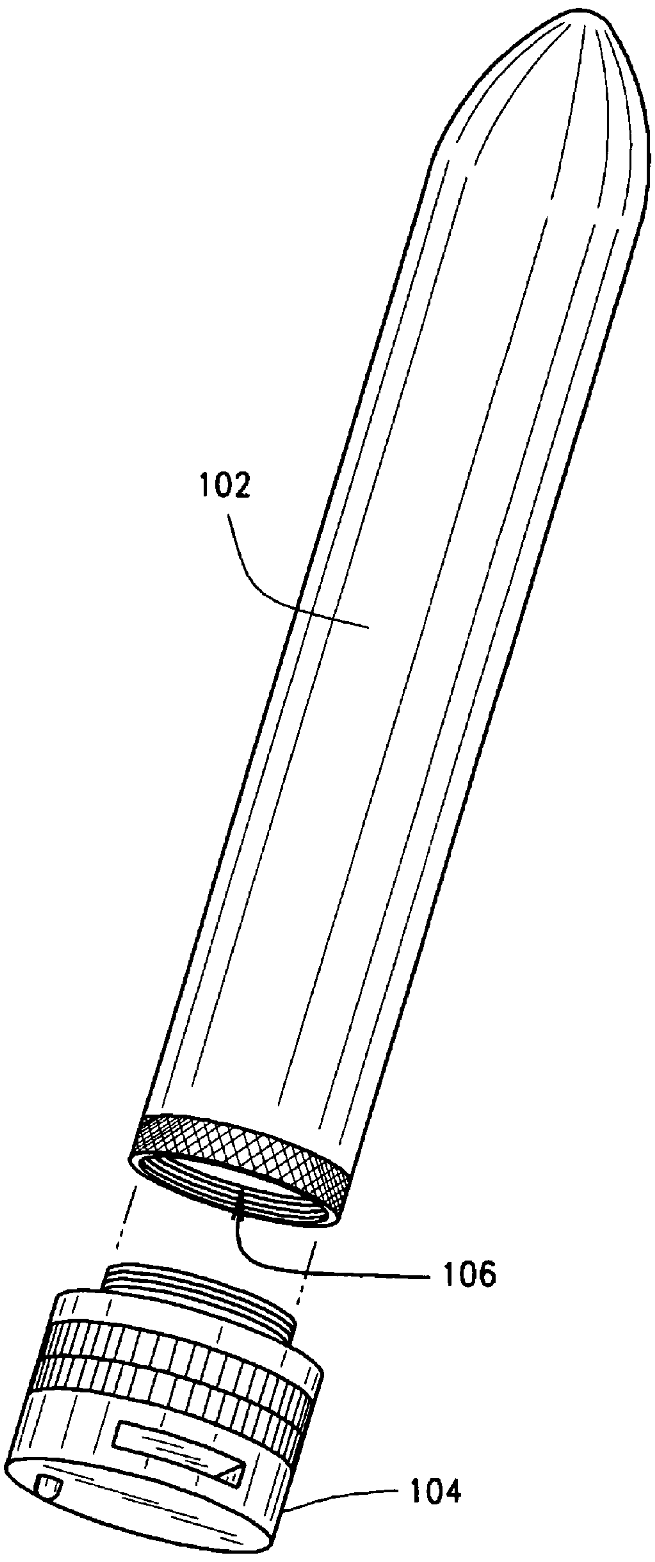
FIG. 3 is an exploded perspective view looking into the housing of the phallic device shown in FIGS. 1 and 2 with the end cap removed from the housing.

Referring now to FIGS. 1 through 3, there is shown a phallic device, generally indicated by reference number 100 according to one embodiment of the present invention. As shown, the phallic device 100 includes a housing 102 and an end cap 104.

The outside of the housing 102 is generally phallic-shaped so as to resemble the form (if not the size) of a human penis. The housing 102 can be provided in various sizes and colors. In addition, a wide range of materials can be used for the housing 102, including rubber, gel foams, plastics, silicone, and other suitable materials. In various embodiments, the housing 102 is configured (e.g., sized, shaped, colored, formed of a material, etc.) in a manner similar to existing commercially available dildos and vibrators. As described herein, various embodiments include an end cap that is retrofit onto an existing dildo or vibrator.

Figure 8:
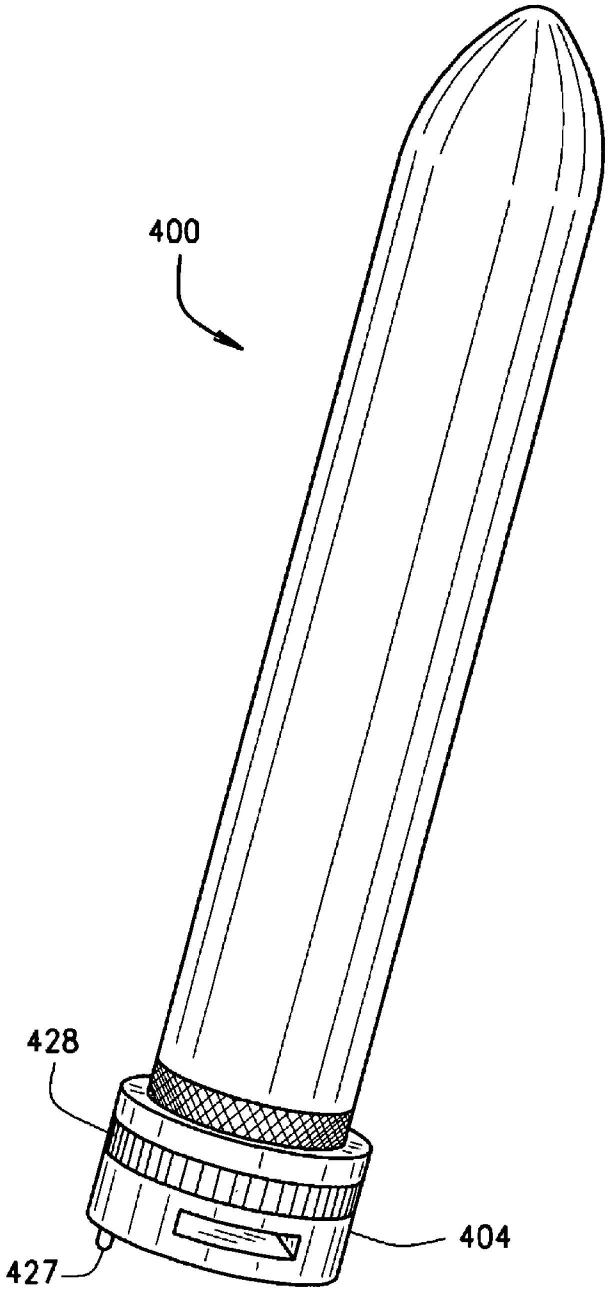
FIG. 8 is a perspective view of a static or non-vibrating phallic device including an end cap having an audio system according to another embodiment of the present invention.
Figure 9:
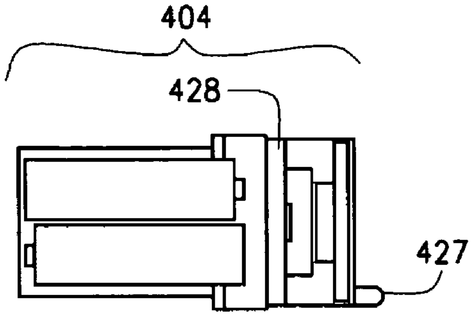
FIG. 9 is a schematic of the end cap shown in FIG. 8 and further illustrating the end cap's audio system and batteries for providing electrical power for operating the audio system.
Figure 9:
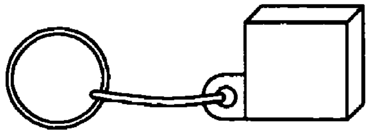

As shown in FIGS. 2 and 3, the housing 102 defines a generally hollow cavity 106 in which is positioned a motor 108 and batteries 110 for providing electrical power for operating the motor 108. When electrically connected to the batteries 110, the motor 108 causes the housing 102 to vibrate. Accordingly, the phallic device 100 of this embodiment is a portable handheld "vibrator". Alternatively, other embodiments do not include a vibration-causing motor, such as the static or non-vibrating phallic device or dildo 400 (FIGS. 8 and 9) that includes an end cap 404 having an audio system. As shown in FIGS. 8 and 9, the dildo end cap 404 includes a push-button switch 427 for turning on/off the audio system, and a volume control switch 428 in the form of a rotatable annular ring.

FIG. 2 illustrates two AA batteries 110 positioned with the housing 102. Alternatively, other suitable power sources can be used for providing the electrical power to the motor 108, including other battery types, battery sizes, renewable batteries, rechargeable batteries, disposable batteries, etc. In some embodiments, the motor 108 can receive electrical power from a power source external to the housing 102. For example, the housing 102 may include an AC adapter port into which an electrical cord is plugged such that the motor 108 receives electrical power through the electrical cord from a standard wall outlet. Or, for example, the motor 208 within the housing 202 can receive electrical power via connectors 218 from one or more batteries 210 within the end cap 204, as shown in the phallic device 200 of FIG. 6.

Figure 4:
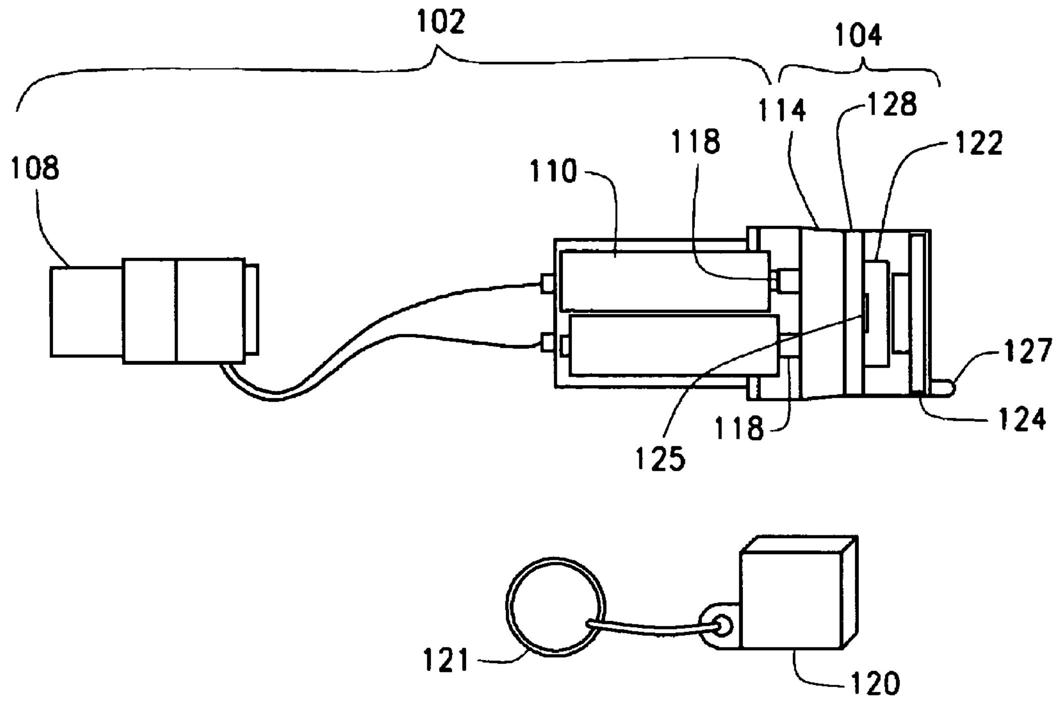
FIG. 4 is a schematic of the phallic device shown in FIGS. 1 through 3 and illustrating the end cap's audio system.
Figure 5:
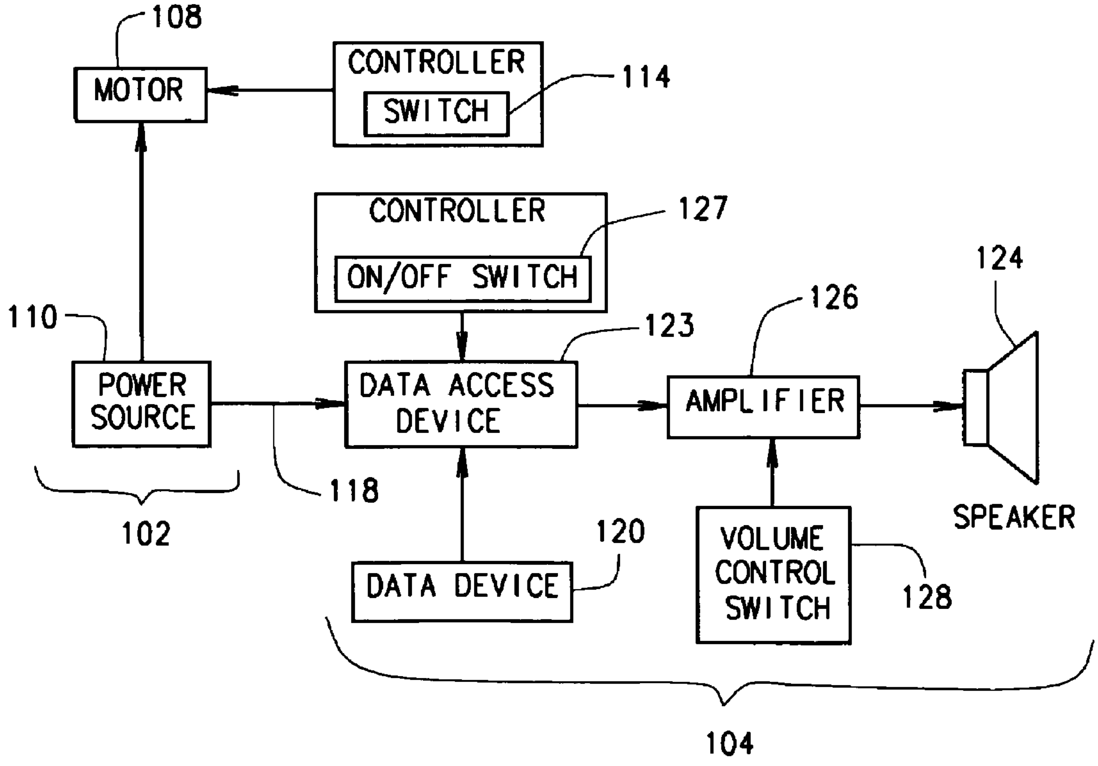
FIG. 5 is a block diagram illustrating the audio system and control circuitry for controlling operation of the phallic device shown in FIG. 1.

With further reference to FIGS. 1 through 5, the phallic device 100 includes at least one switch for controlling operation of the motor 108. As shown in FIGS. 4 and 5, the phallic device 100 includes the switch 114 for switchably connecting the motor 108 to the batteries 110. The switch 114 may also allow the user to adjust the rate of speed and/or manner of vibration. Alternatively, the phallic device may include a first "ON/OFF" switch for activating and deactivating the vibration-generating motor, and a second "variable speed switch" switch for controlling the rate and/or type of vibration. In other embodiments, the vibration may be constant such that the switch 114 is only used to turn on or turn off the vibration features.

In addition, various embodiments include the switch 114 being used to control the operation of the audio features as well. That is, the manner in which the operation of the vibration feature is controlled may also be used for controlling operation of the audio system. Alternatively, and as shown in the figures and described herein, there may be separate (or at least partially separate) systems for controlling the operation of the audio features and the vibration feature. Various embodiments includes means (e.g., switch 114, etc.) for controlling operation of the vibration feature that is entirely independent and distinct from the means (e.g., on/off push-button switch 127, volume control switch 128, etc.) for controlling operation of the audio features.

As shown in FIGS. 1 through 4, the end cap 102 includes the switch 114 for controlling operation of the motor 108. In the illustrated embodiment, the switch 114 is a rotationally adjustable annular ring that is provided on the end cap 104. By rotating the ring relative to a longitudinal centerline axis of the device 100, the user can control the operation of the motor 108. For example, the user can rotate the ring to turn on/off the motor 108, and/or adjust the vibration speed (increase or decrease) depending on the direction and amount of rotation of the ring 114. Alternatively, the rotationally adjustable ring 114 can be disposed around a portion of the housing 102. In addition, other suitable switches can be implemented for controlling operation of the motor 108, including push-button switches, electrical terminals (e.g., externally disposed on the end cap 104 or housing 102) for switchably connecting the motor 108 to the batteries 110 when the electrical terminals are placed in contact with the user's body, motion-responsive switches, light-sensitive switches, temperature-sensitive switches, compression switches, voice activated switches, etc. For example, a push-button switch may be provided on the end cap and/or the housing that allow the user to turn on/off the vibration feature and/or cycle through various vibration modes by successively pressing the push-button switch.

Figure 13:
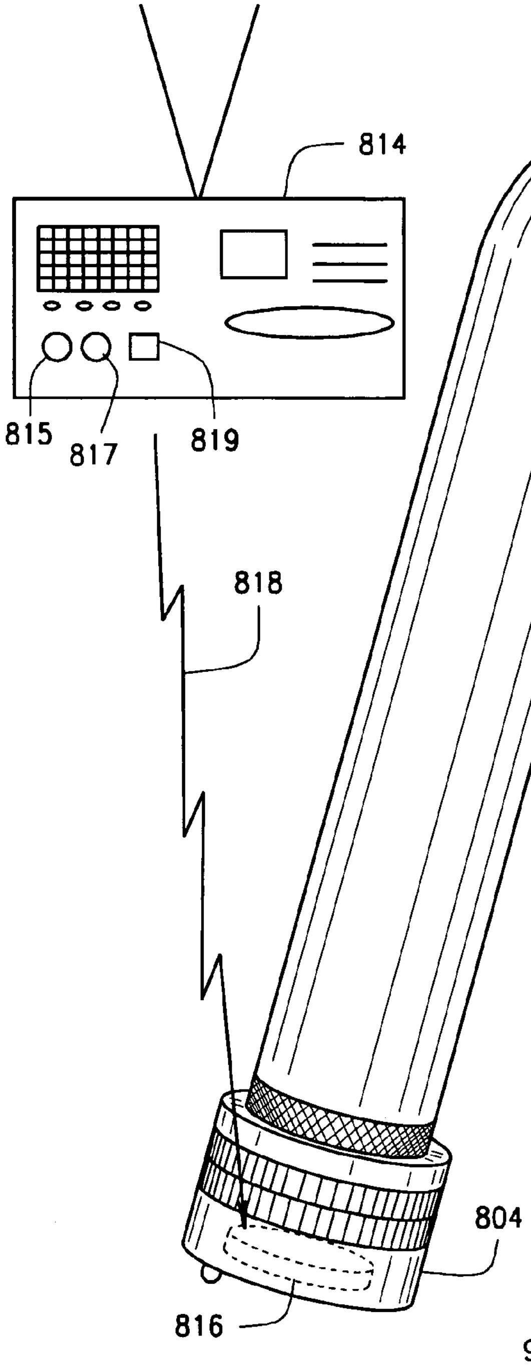
FIG. 13 is a perspective view of a phallic device having an end cap with an audio system and illustrating a remote control device for controlling operation of the phallic device according to another embodiment of the invention.

Further embodiments include a remote control device that can be used to control the operation of the vibration-generating motor and/or audio system. For example, FIG. 13 illustrates a phallic device 800 which is remotely controllable with an external transmitter or remote control device 814. The phallic device 800 includes a controller 816 within the end cap 804 (although the controller 816 can also be positioned within the housing 802 or at other suitable locations). The controller 816 is capable of receiving signals 818 from the remote control 814. In some embodiments, the controller 816 receives signals 818 (wirelessly) from the remote control device 814 (e.g., wireless signals communicated between antennae, electromagnetic wave energy, cellular phone, RF energy or radio transmissions, etc.). Other embodiments include the remote control device 814 being wired to the phallic device 800 such that the controller 816 receives signals 818 from the remote control device 814 through one or more wire(s) connecting the remote control device 814 to the phallic device 800. In such embodiments, the remote control device 814 can also include batteries (or other suitable power source) that provide electrical power to the device 800 through the wire(s).

Signals 818 received by the controller 816 provide information to the controller 816 for causing the controller 816 to select a particular vibration mode (e.g., on/off, fast vibrations, slow vibrations, pulsating, wave, randomly changed rhythms, etc.). Accordingly, the vibration mode can thus be remotely controlled by a user via the external remote control 814. As described herein, various embodiments also or alternatively include the remote control device being used to remotely control the audio features as well. In FIG. 13, the remote control 814 includes a first button 815 for controlling operation of the vibration-generating motor, and a second button 817 for controlling operation of the audio system within the end cap. The remote control 814 can also include an audio system (e.g., one or more computer chips 819) for playing audio, such as prerecorded messages or music.

Referring back to FIGS. 1 through 5, the end cap 104 and its audio system will now be described. As shown, the end cap 104 is threadably engaged to the housing 102. Accordingly, the end cap 104 can be readily removed from the housing 102 if the user wants to access the cavity 106 within the housing 102, for example, to replace the batteries 110. Alternatively, other suitable fastening methods can be employed for removably engaging the end cap 104 to the housing 102. In yet other embodiments, the end cap 104 is fixedly attached to or integral with the housing 102. In various embodiments, a waterproof seal is formed between the end cap 104 and housing 102 when the end cap 104 is engaged to the housing 102.

Figure 6:
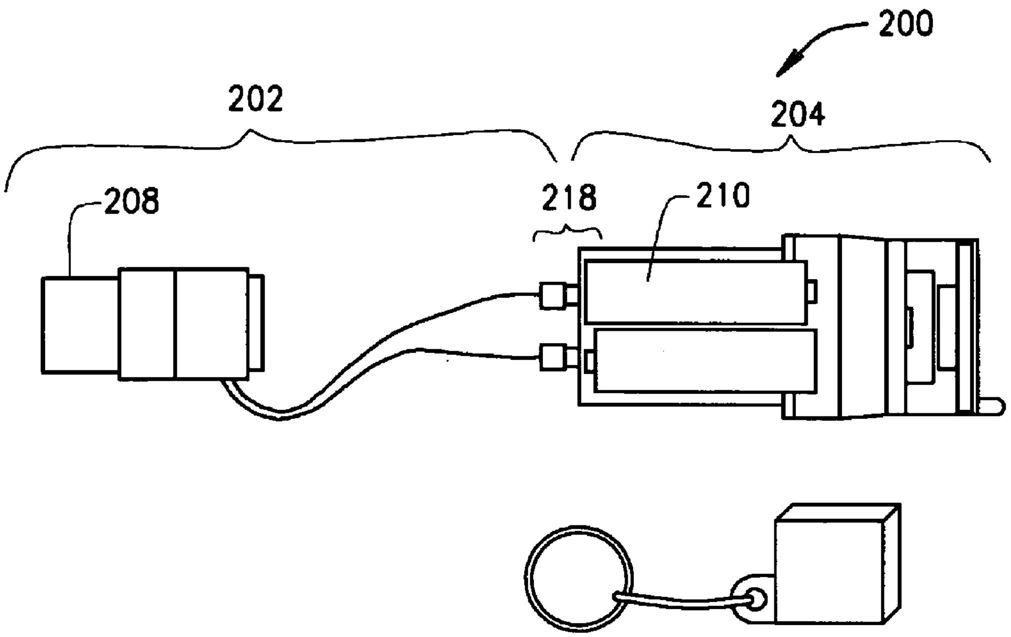
FIG. 6 is a schematic of another embodiment of a phallic device end cap having an audio system, wherein the end cap includes batteries for providing electrical power for operating the audio system and for operating a vibration-generating motor within a housing of the phallic device.
Figure 7:
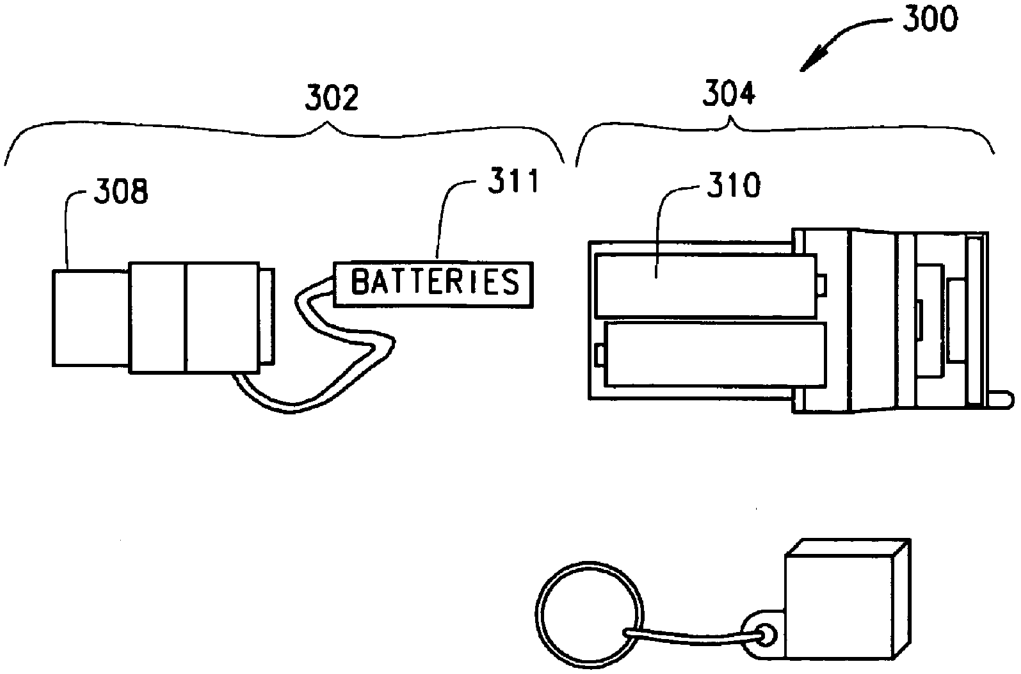
FIG. 7 is a schematic of another embodiment of a phallic device end cap having an audio system and batteries for providing electrical power for operating the audio system, and wherein the vibration-generating motor receives electrical power from a separate set of batteries within the housing.

The end cap 104 includes an audio system. The end cap 104 also includes connectors 118 for switchably connecting the audio system to the batteries 110 when the end cap 104 is threadably engaged to the housing 102. As shown in FIG. 2, two AA batteries 110 are positioned with the housing 102. Alternatively, other suitable power sources can be used for providing the electrical power to the audio system, including other battery types, battery sizes (e.g., watch batteries, etc.), renewable batteries, rechargeable batteries, disposable batteries, etc. In some embodiments, the motor 108 and audio system receive electrical power from different power sources. For example, FIG. 6 illustrates an embodiment in which the end cap 204 includes batteries 210 for providing electrical power for operating the audio system and the vibration-generating motor 208. Or, for example, FIG. 7 illustrates an embodiment in which the end cap 304 includes batteries 310 for providing electrical power for operating the audio system, but the vibration-generating motor 308 receives electrical power from a separate set of batteries 311 within the housing 302. In other embodiments, the audio system can receive electrical power from a power source external to the phallic device. As yet another example, the end cap may include an AC adapter port into which an electrical cord is plugged such that the audio system receives electrical power through the electrical cord from a standard wall outlet.

The audio system includes means for accessing audio data from a data device. The audio system also includes means for producing audio (e.g., voice messages, music, instructions, other sounds, etc.) corresponding to the audio data. As shown in FIG. 5, the means for accessing audio data comprises data access device 123, and the means for emitting sound comprises speaker 124.

In the illustrated embodiment of FIGS. 2, 4, and 5, the data device comprises a MASK ROM (read only memory) cartridge 120 sized to be received within a cartridge insert slot or opening 122. As shown in FIG. 4, an edge connector 125 is positioned within the slot 122. Accordingly, when the cartridge 120 is positioned within the slot 122, audio data on the cartridge 120 is accessible to a data access device 123 within the end cap 104. Optionally, the cartridge 120 can be provided with a key ring 121, or other suitable device for assisting the user in removing the device from the slot 122.

Figure 11:
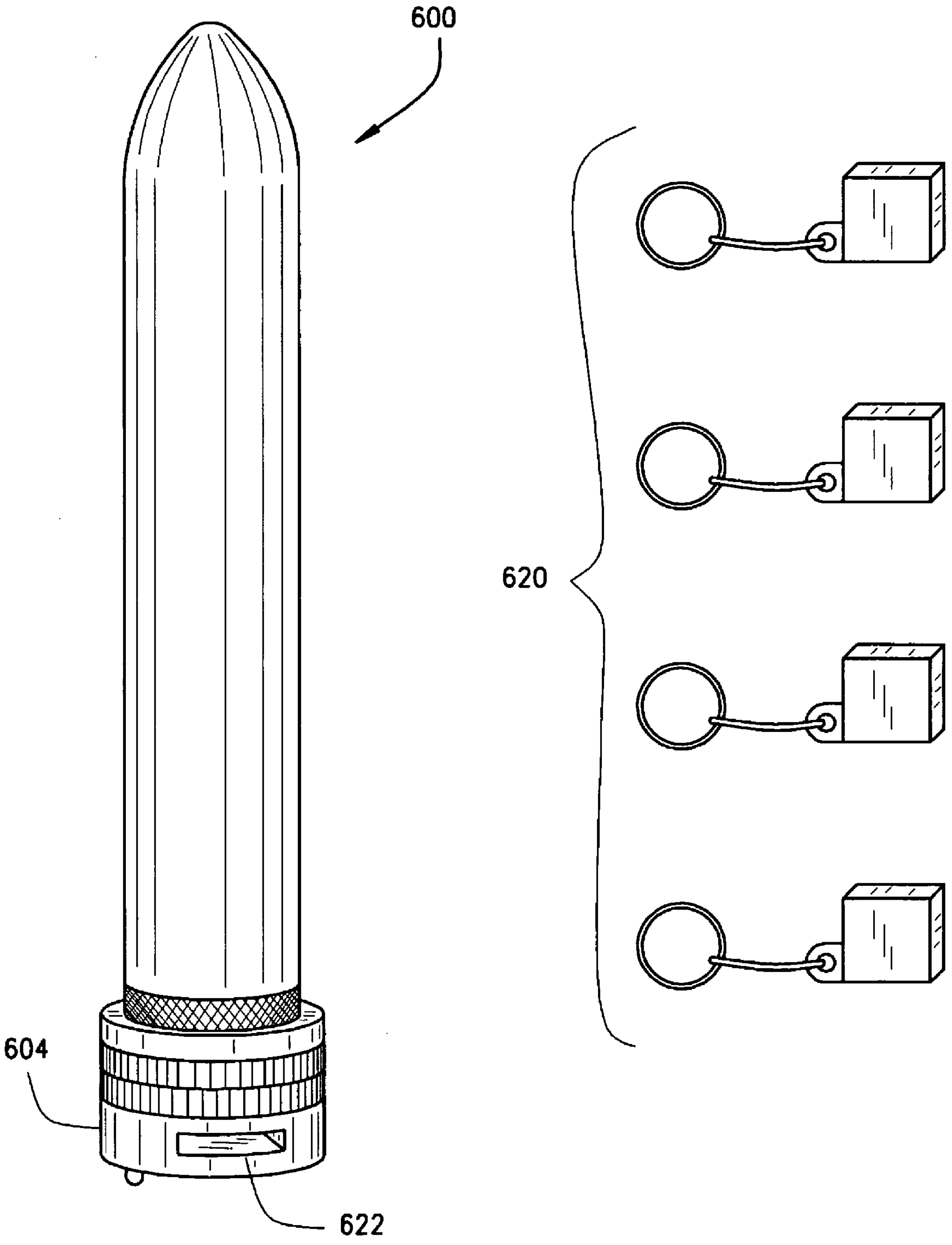
FIG. 11 is a perspective view of a phallic device and a plurality of interchangeable data devices each having audio data such that a user can choose which audio is played by selecting from amongst the data devices.

As shown in FIG. 11, a plurality of interchangeable MASK ROM cartridges 620 (or other data devices) may be provided in order to enable a user to select which audio is played by the end cap 604 of the phallic device 600. Each cartridge 620 has different audio data thereon such that the particular audio played will be determined by which cartridge 620 is positioned in the slot 622. Accordingly, the user can change the audio by removing an existing cartridge 620 from the slot 622, if there is one, and then inserting another cartridge 620 into the slot 622.

Alternatively, other data devices can be used with a phallic device of the present invention. Exemplary data devices include flash memory cards, memory sticks, other ROM storage devices, other computer readable media for storing audio, random access memory (RAM), read/writable data devices, etc. The particular type/form of data device used can depend, for example, on the particular type/form data access device within the end cap. Conversely, the particular type/form of data access device within the end cap can depend, for example, on the particular type/form data device(s) to be used. In various embodiments, the data device and data access device are relatively small so that the phallic device remains a portable hand-held device.

Various embodiments include writable data devices such that a user can modify (e.g., add, delete, update, re-record, etc.) audio data of the writable data device. In some embodiments, a user can create personal, individualized, customized personal messages that are written to the data device, wherein the personal messages can be then be played during use of the phallic device. For example, personalized messages can be played one after another without interruption even though the messages were created or recorded at different times. The user can also delete or update messages, for example, by recording new or more current messages. In various embodiment, the personalized messages can be played simultaneously with prerecorded audio. For example, recorded voice messages may be played with background prerecorded music.

Figure 15:
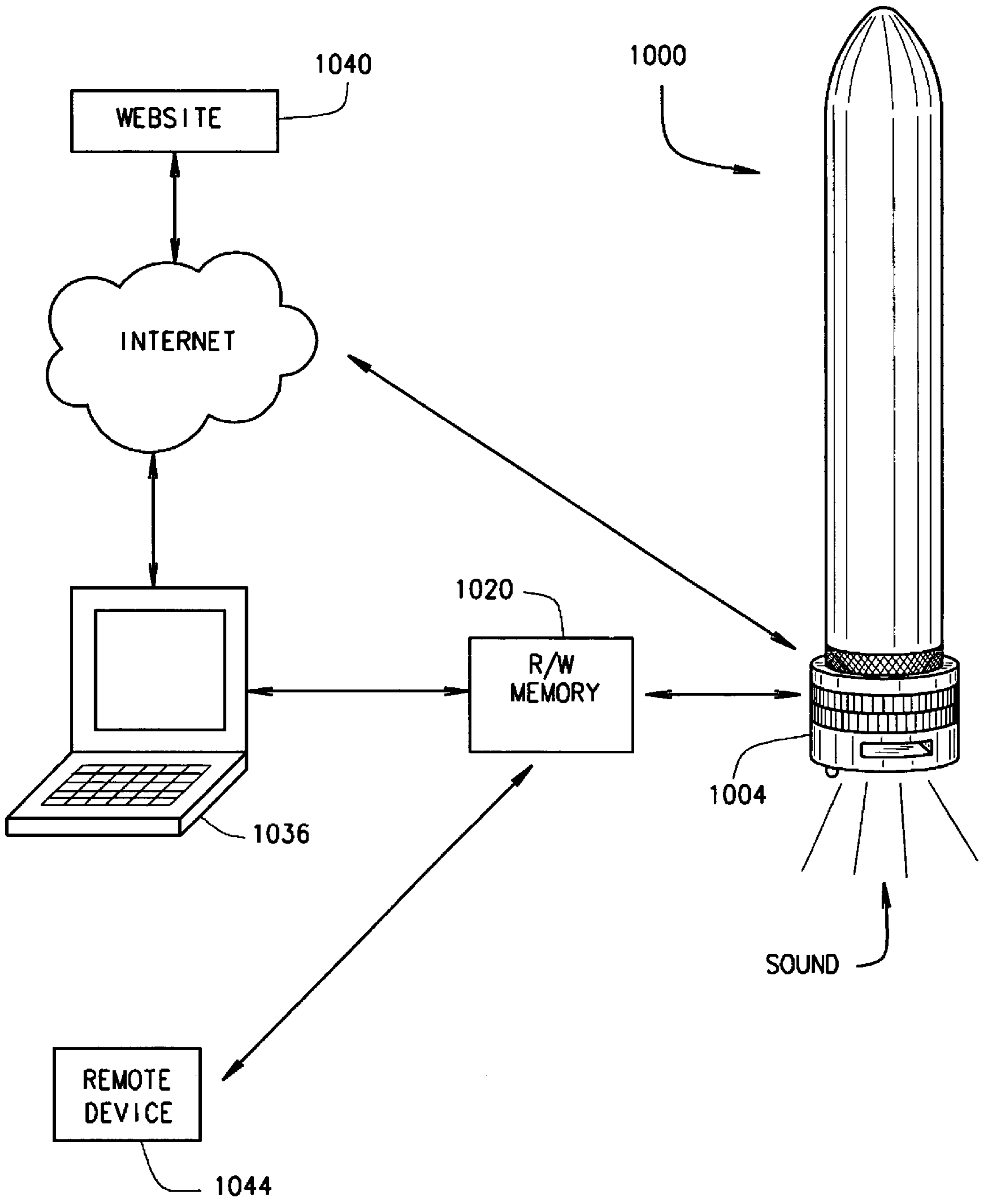
FIG. 15 is a block diagram illustrating a system and method for personalizing or customizing audio to be played by a phallic device according to another embodiment of the invention.

Various embodiments allow a user to customize audio data by selectively downloading audio data from an Internet website to a data device for later playback by the phallic device. For example, and as shown in FIG. 15, a user can first-remove a read/write data device 1020 from the end cap 1004 (or use a blank data device 1020), and insert the data device 1020 into a data device slot of a network device 1036 (e.g., personal desktop or laptop computer, etc.). The user can then use the network device 1036 to access an Internet website 1040, and select audio data therefrom that is downloaded to the data device 1020. Or, for example, a user may download data stored on the network device 1036 to the data device. In either case, after downloading, the user can position the data device 1020 into the slot of the end cap 1004 such that the downloaded audio data can be accessed and played by the phallic device 1000.

Also shown in FIG. 15, the data device 1020 can be used with a remote device 1044, wherein the remote device 1044 records a user's voice and then writes audio data corresponding to the recorded voice to the data device 1020. In one particular embodiment, the remote device 1044 comprises a cradle or voice recorder (which may be relatively small such as three inches by four inches, etc.) to allow the user to customize the audio on the chip, cartridge, or other data device 1020. In such embodiments, a user can remove an existing data device 1020 from the end cap 1004 or use a blank data device 1020. The user then inserts the data device 1020 into a data device slot of the remote device 1044. The remote device 1044 records the user's voice message(s) and writes corresponding audio data to the data device 1020. The user can remove the data device 1020 from the remote device 1044, and position the data device 1020 into the slot of the end cap 1004 such that the recorded voice messages can be accessed and played. In further embodiments, the end cap can include a microphone that records the user's voice, with audio data corresponding thereto being written to the data device for subsequent playback.

Accordingly, the cradle or other remote device 1044 permits users the opportunity to customize their own recordings in addition, or as an alternative, to relying on the Internet for making custom recordings. But when custom recordings are made "offsite" (given from one person to another from a remote location), the Internet can be used for making the custom recordings used in conjunction with the "cradle" and a hot wire. Additionally, or alternatively, various embodiments will also permit the user to coordinate a telephone recording with an Internet website as a means of making the customized voice modules and recordings. By way of example only, various embodiments can include one or more of the systems for producing voice messages described in U.S. Pat. No. 5,570,414 entitled "Voice Message Keepsake System"; U.S. Pat. No. 5,490,206 entitled "Voice Message Keepsake System"; U.S. Pat. No. 5,425,078 entitled "Voice Message Keepsake System"; and/or U.S. Pat. No. 6,356,626 entitled "Point to Point Voice Message Processor, Method and Recording/Playback Device".

The ability to record personal messages can provide several advantages. For example, an individual purchaser may record personal messages, and then give the phallic device with the personally recorded messages as a gift to a lover. This provides users with the opportunity to re-record messages over existing personal messages and keep these messages fresh or current by updating the messages periodically. The ability to leave customized messages which are later played while using the phallic device can perhaps heighten the sexual response.

In the illustrated embodiment, the data device 120 is removable from the end cap 104. In other embodiments, however, the data device 120 may be integrated into or fixedly disposed within the end cap 104. For example, other embodiments include playback circuitry (and record circuitry in some embodiments) mounted on a printed circuit board, which is disposed within the end cap 104. In such embodiments, the computer chip(s) include audio data that is communicated to a sound emitter (e.g., speaker). In response, the sound emitter emits audio consistent with the audio data from the computer chip(s). In one embodiment, the end cap 104 includes a plurality of computer chips, and at least one controller (e.g., rotary switch, etc.) for allowing the user to select from amongst the plurality of computer chips. By selecting a particular computer chip, the user is thus able to select which audio is played. Additionally, or alternatively, a phallic device may include means (e.g., wireless, wired, combinations thereof) for connecting or linking to a network (e.g., the Internet, etc.) to download audio data from the Internet for playback by the audio system within the end cap. In various embodiments, the phallic device includes one or more of the audio features for enabling customized recordings described in U.S. Pat. Nos. 5,570,414; 5,490,206; 5,425,078; and/or U.S. Pat. No. 6,356,626. Alternatively, other suitable audio features can be included within the end cap for enabling customized recordings.

As shown in FIG. 5, the sound emitter comprises a speaker 124 within the end cap 104. The speaker 124 is connected to an amplifier 126 (FIG. 5). In one particular embodiment, the speaker 124 is generally circular and has a diameter of about thirty-six millimeters. Alternatively, other shapes, sizes, and types of speakers can be used, depending, for example, on the particular shape and size of the end cap 104.

In various embodiments, the level of sound emitted by the speaker 124 can be adjustably controlled by a volume control, e.g., rheostat. In the illustrated embodiment, the volume control is a rotationally adjustable annular ring 128 (FIGS. 1 and 5) provided on the end cap 104. By rotating the ring 128 relative to a longitudinal centerline axis of the phallic device 100, the user can increase or decrease the volume depending on the direction of rotation of the ring 128. Alternatively, other suitable switching mechanisms can be used for controlling the sound volume of the speaker. For example, a wired or wireless remote control device can be provided that is used to control the volume of the speaker.

The phallic device 100 further includes at least one switch 127 for switchably connecting the audio system to the batteries 110. As shown in FIGS. 1 and 3, the phallic device 100 includes three switches, namely, the vibration control switch 114, the audio system on/off switch 127, and the volume control switch 128. In this particular illustrated embodiment, the switches 114 and 128 are annular rotational rings, and the switch 127 is a push-button switch. Alternatively, other switching mechanisms and arrangements can be implemented. For example, another embodiment includes a rotationally adjustable annular ring provided on the end cap (or the housing) that is rotatable relative to a longitudinal centerline axis of the phallic device. By rotating this ring, the user can turn the audio system on/off and increase/decrease the volume depending on the rotational direction of the ring.

Further embodiments include other suitable switches for controlling operation of the audio system, such as push-button switches, electrical terminals (e.g., externally disposed on the end cap 104 and/or housing 102) for switchably connecting the audio system to the batteries 110 when the electrical terminals are placed in contact with the user's body, motion-responsive switches, light-sensitive switches, temperature-sensitive switches, compression switches, voice activated switches, etc. One exemplary embodiment includes a push-button switch provided on the end cap and/or the housing that allows the user to turn on/off the audio system and to also cycle through different audio (e.g., cycle through different computer chips, different data devices within the end cap, etc.) by successively pressing the push-button switch.

Further embodiments include a remote control device that can be used to control the operation of the vibration-generating motor and/or audio features. For example, FIG. 13 illustrates a phallic device 800 which is remotely controllable with an external transmitter or remote control device 814. The phallic device 800 includes a controller 816 within the end cap 804, although the controller 816 can also be positioned within the housing 802 or at other suitable locations. The controller 816 is capable of receiving signals 818 from the remote control 814. In some embodiments, the controller 816 receives signals 818 (wirelessly) from the remote control device 814 (e.g., wireless signals communicated between antennae, electromagnetic wave energy, cellular phone, RF energy or radio transmissions, etc.). Other embodiments include the remote control device 814 being wired to the phallic device 800 such that the controller 816 receives signals 818 from the remote control device 814 through one or more wire(s) connecting the remote control device 814 to the phallic device 800. In such embodiments, the remote control device 814 can also include batteries (or other suitable power source) that provide electrical power to the device 800 through the wire(s).

Signals 818 received by the controller 816 provide information to the controller 816 for causing the controller 816 to turn on/off the audio system and/or to select the particular audio to be played by the audio system. Accordingly, the operating mode for the audio system can thus be remotely controlled by a user via the external source 814. As described herein, various embodiments also or alternatively include a remote control device that allows the user to remotely control the vibration features, if any, of the phallic device. In FIG. 13, the remote control 814 includes a first button 815 for controlling operation of the vibration-generating motor, and a second button 817 for controlling operation of the audio system within the end cap. The remote control 814 can also include an audio system (e.g., one or more computer chips 819) for playing audio, such as prerecorded messages or music.

Other aspects of the invention provide an end cap that can be retrofit onto an existing dildo, vibrator, or other sexual device in order to provide audio features to the existing dildo/vibrator, thereby increasing its functionality and commercial appeal. For example, an existing end cap of the phallic device can be removed and replaced with an end cap having an audio system. In one embodiment, the end cap having the audio features includes a threaded portion that is compatible with the threads of the existing vibrator housing. A standard vibrator can thus become a talking or other sound-producing phallic device by simply removing (e.g., unscrewing, etc.) the original end cap from the vibrator and threadably engaging an end cap of the present invention onto the vibrator. To accommodate the audio system, the retrofittable end cap may be slightly larger than the existing end cap. The end cap can include one or more computer chips for playing personalized voice messages, instructions, music, natural sounds, artificial sounds, etc. In some embodiments, the computer chip(s) can also allow the user to create and/or recreate personalized audio, such as voice messages and instructions.

The retrofitted end cap can also include a switch for controlling operation of the vibration feature (e.g., turn on or off, increase or decrease vibration speed, change rhythm or pulsations of vibrations, etc.). Accordingly, the vibrator is still able to perform all of its original functions but now has audio capabilities by way of the retrofitted end cap. Accordingly, these embodiments can convert an existing vibrator having a user-controllable vibration feature (e.g., activating, deactivating, adjusting the speed, rhythm, etc.) into a more desirable product by retrofitting an end cap that not only maintains that user control of the vibration feature, but which also provides an audio feature by which the user can play personally recorded and/or prerecorded messages.

In various embodiments, audio can be coordinated with the external appearance of the phallic device. For example, the phallic device housing can be provided in a particular color so as to resemble the skin color of a person of a particular nationality. In such embodiment, the audio may include prerecorded messages with speech inflections, patterns, accents, foreign language, stereotypical grammar, etc. associated with the nationality that the phallic device housing is intended to resemble. Or, for example, the phallic device housing can be tiger-striped in color, and the audio can include prerecorded messaging of a tiger roaring. As yet another example, the phallic device can be sized, shaped, and colored consistent with an elephant's penis, and the audio can include prerecorded elephant sounds. Such features may further increase the commercial appeal of these phallic devices, for example, as gag gifts.

Figure 10:
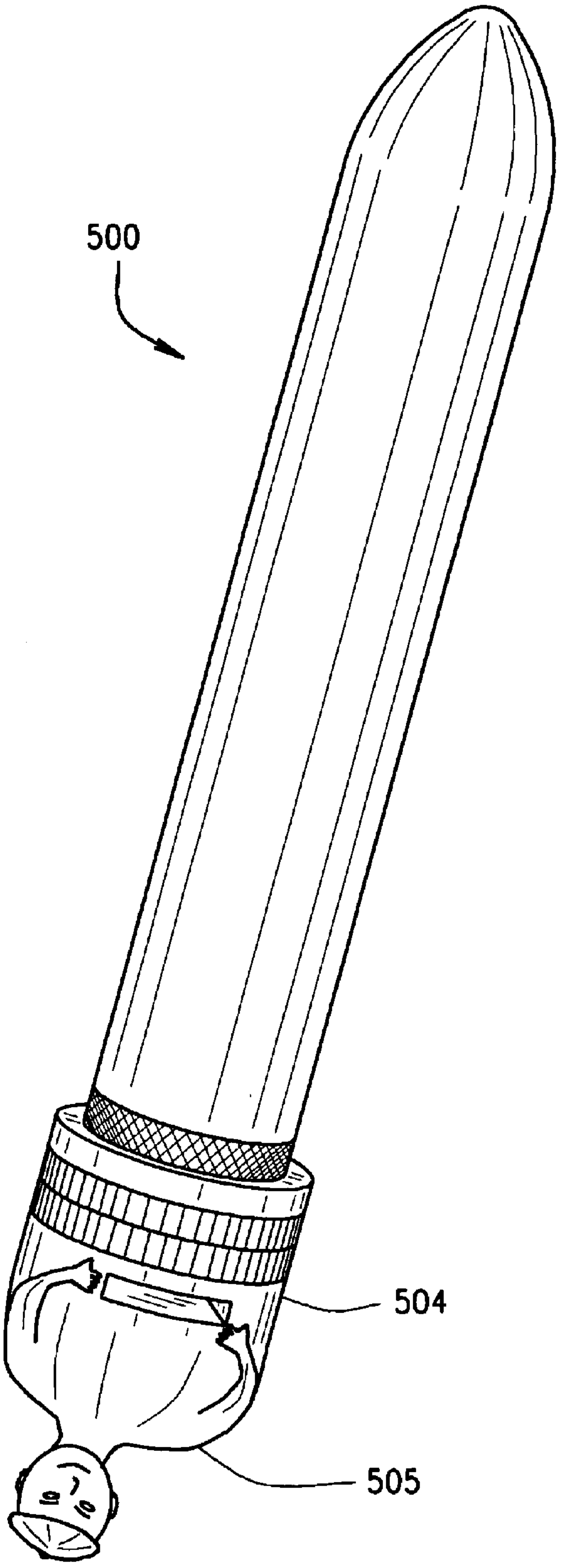
FIG. 10 is a perspective view of a phallic device including an end cap having an audio system wherein the end cap's outer surface is configured to resemble a figurine.

In various embodiments, the end caps can be configured (e.g., shaped, sized, colored, etc.) to resemble recognizable objections, such as a caricature or figurine of a famous person, the recipient of the device as a gag-gift, or an end-user of the device. The audio may include prerecorded messages coordinated with the recognizable object. For example, FIG. 10 illustrates a phallic device 500 having an end cap 504 shaped as a figurine 505. The phallic device is configured to play voice messages with speech inflections, patterns, accents, foreign language, stereotypical grammar, etc. associated with the particular figurine that the end cap resembles. In one exemplary embodiment, the figurine can resemble a French chamber maid or a person wearing a French beret, and the audio can include prerecorded voice messages in the French language or in English but with a French accent. As yet another example, a figurine would be a replica of former President Bill Clinton, with the audio effectively mimicking former President Clinton's speech inflections. The functionality of the end cap could be the same as described herein. In further examples, the end cap can be customized for a particular customer such that the end cap resembles the particular customer. In such embodiments, the audio can include messages personally created by the customer. In which cases, the audio emitted by the device matches the voice of the person that the end cap resembles.

Figure 12:
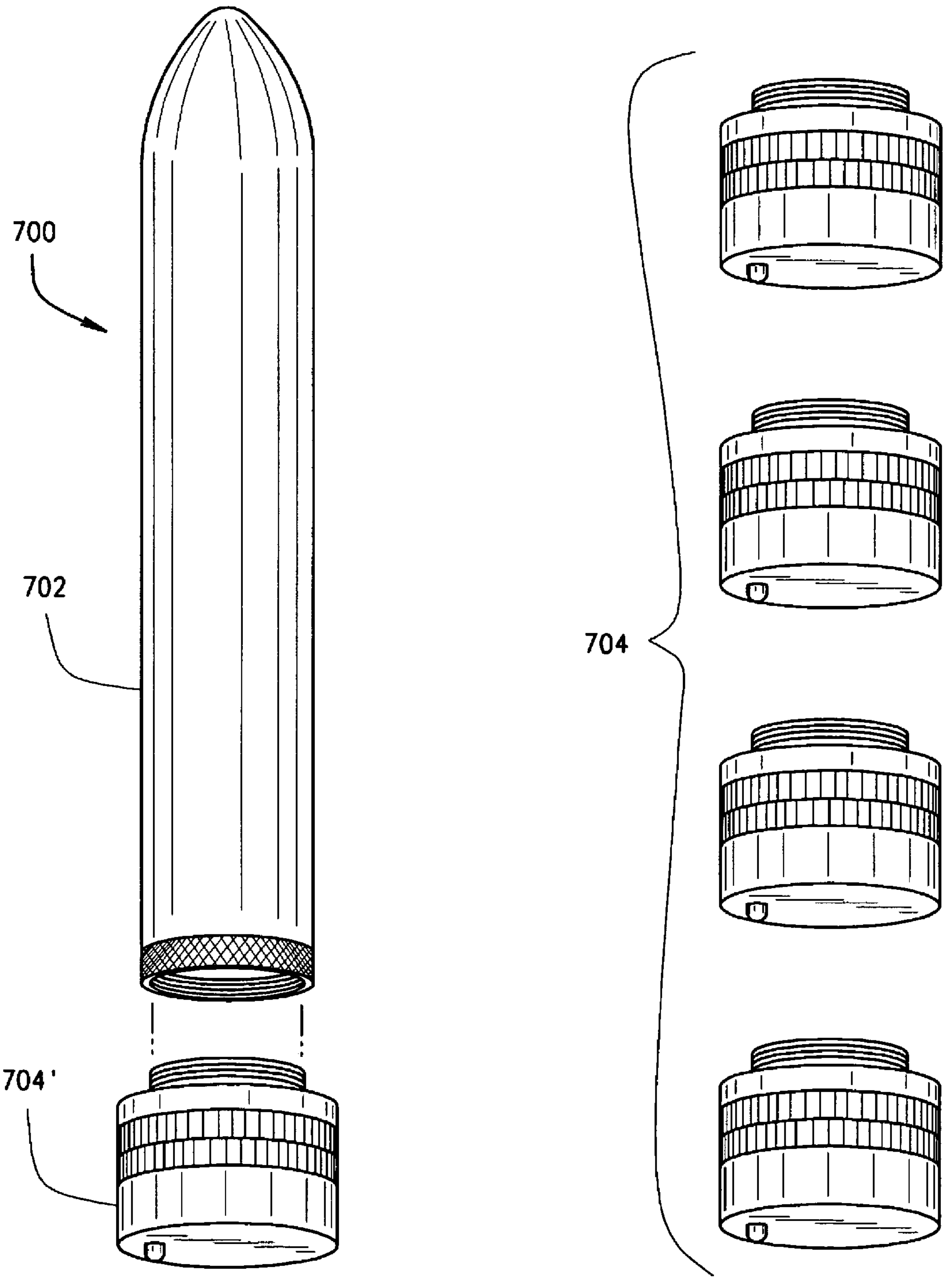
FIG. 12 is a perspective view of a phallic device and a plurality of interchangeable end caps each having a data device with audio data such that a user can choose which audio is played by selecting and then attaching the selected end cap to the phallic device.

FIG. 12 illustrates a plurality of interchangeable end caps 704 that can be attached to the housing 702 of the phallic device 700. Each end cap 704 includes a data device having audio data and a data access device or means for accessing the audio data. Each end cap also includes a sound emitter or means for emitting audio that corresponds to the audio data. Accordingly, the user can thus select which audio is played by selecting an end cap 704' and then attaching the selected end cap 704' to the phallic device housing 702.

Figure 14:
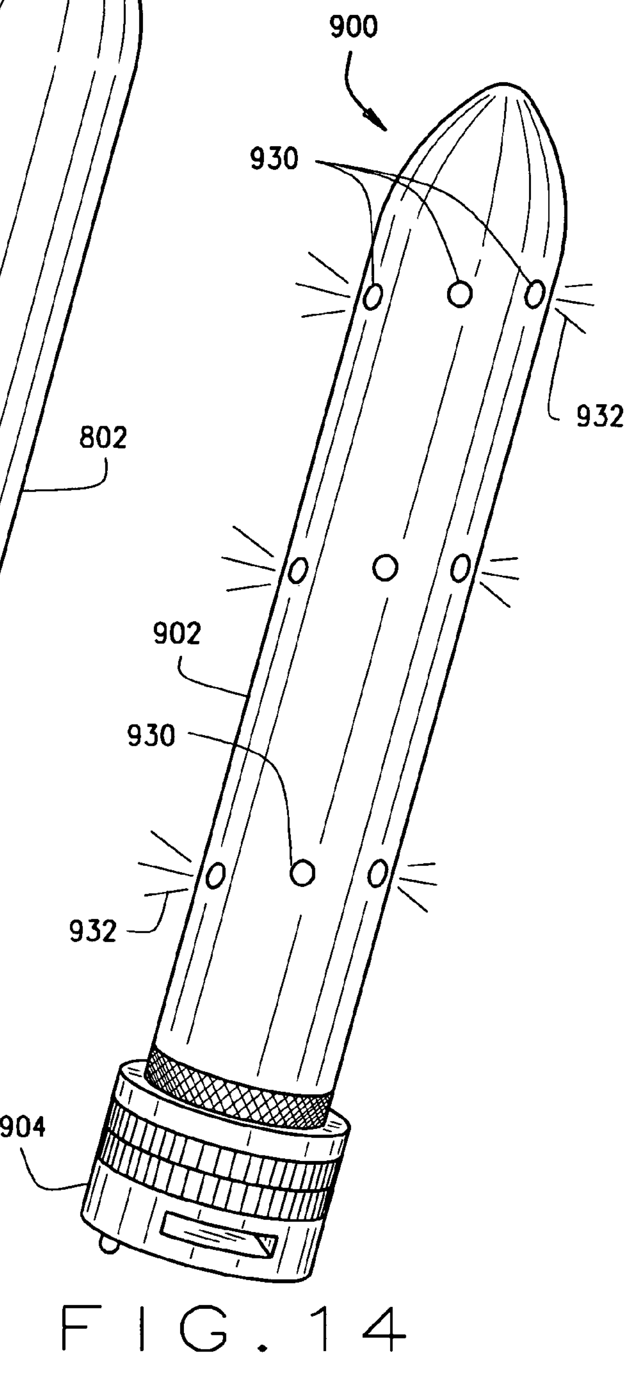
FIG. 14 is a perspective view of a phallic device having LEDs according to another embodiment of the invention.

In various embodiments, a phallic device (e.g., 100, 200, 300, 400, 500, 600, 700, 800, 900, etc.) can also include at least one light source, at least one power source for powering the light source, and at least one switch for switchably connecting the light source to the power source. For example, FIG. 14 illustrates a phallic device 900 having a plurality of light-emitting diodes (LEDs) 930 that when switchably connected to a power source produces light 932 for illuminating the phallic device (or portion thereof). Alternatively, other suitable light sources may be used depending, for example, on the particular application and/or on user preferences. In addition, one or more of the LEDs may produce light that has at least one attribute (e.g., color, intensity, blink speed, hue, saturation, brightness, etc.) different than the light produced by at least one other LED. A lighted phallic device of the present invention can be configured to produce any of a wide range of colored light depending, for example, at least in part on user preferences and/or that is consistent with the audio being played by the phallic device.

The LEDs 930 may be configured to produce thematic light that is coordinated to the audio emitted by the audio system within the end cap 904. For example, the end cap 904 may play music (e.g., stars and stripes, etc.), and the LEDs may produce light 932 that pulsates (e.g., strobe-light effect, etc.) to the beat of the music and/or that is color-coordinated (e.g., red, white and blue, etc.) to the music.

The LEDs 930 can be coupled to (e.g., positioned within or embedded within) the housing 902. The housing 902, in turn, can be translucent or transparent to allow light 932 from the LEDs 930 to be transmitted therethrough. Additionally, or alternatively, LEDs can be coupled to (e.g., positioned within or embedded within) the end cap, and the end cap can be translucent or transparent to allow light from the LEDs to be transmitted therethrough.

The LEDs 930 can receive electrical power from the same power source as does the audio system. Alternatively, the LEDs 930 can receive electrical power from a different power source than the audio system.

The phallic device 900 can also include a controller (e.g., an integrated circuit/printed circuit assembly and at least one switch) for controlling operation of the LEDs 930. In one embodiment, the LEDs 930 are controlled by the same controller and switch as the audio system. Alternatively, the means for controlling operation of the LEDs 930 can be separate and distinct from the means for controlling operation of the audio features.

In some embodiments, a phallic device may include an audio system within the end cap, LEDs, an end cap, and a housing all tailored or configured consistent with a particular theme. For example, another embodiment includes a phallic device configured consistent with a wedding theme such that the outer surface of the housing is configured to resemble a male torso in a tuxedo, the end cap is configured to resemble the male's head, the audio system plays a bridal march, and LEDs pulsate to the bridal march music. This particular wedding theme-oriented phallic device might then make an excellent gag-gift at a bachelorette party.

Or, for example, one embodiment includes a Halloween-oriented phallic device in which LEDs produce orange and black light display, the outer surface of the housing is configured to resembles a skeletal bone, the end cap is configured to resemble a jack-o-lantern, and the audio system plays spooky or scary music. This Halloween-oriented phallic device might then make an excellent gag-gift or attendance prize at a Halloween party.

In various embodiments, a phallic device having one or more of the audio features described herein also includes means (e.g., wireless, wired, combinations thereof) for connecting or linking to an Internet website. The phallic device includes a controller (e.g., within the end cap and/or housing) capable of receiving signals from the Internet website. The signals received by the controller provide information to the controller for causing the controller to select a particular operating mode (e.g., on/off, fast vibrations, slow vibrations, pulsating, wave, randomly changed rhythms, etc.) for the vibration feature and to control what audio is played by the audio system within the end cap. In various embodiments, the vibrations and audio can be controlled so as to coordinate with what is being visually displayed at the Internet website on the user's computer screen.

In various embodiments, a phallic device having one or more audio features (e.g., recording and/or playback features described herein) can also include one or more ornaments or decorations coupled to the outer surface of the end cap and/or housing. For example, one particular embodiment of a phallic device includes end cap having audio features and an outer surface decorated with costume jewelry (e.g., cubic zirconium, plastic replicas of rubies, emeralds, etc.) on the end cap.

The teachings of the present invention can be applied in a wide range of devices, including vibrators, vibrating dildos, static or non-vibrating dildos, among other sexual toys and novelty toys. Accordingly, the specific references to vibrators and dildos should not be construed as limiting the scope of the present invention to any specific form/type of sexual toy or device.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for sexual stimulation comprising:

a phallic device comprising: a housing, at least one end cap attached to the housing, the at least one end cap including at least one opening for removably receiving a corresponding one of a plurality of interchangeably removable data devices, a data access device for accessing audio data from the interchangeably removable data device within the at least one opening, and, a sound emitter for emitting audio corresponding to the audio data accessed by the data access device from the data device, and the audio is playable by selectively positioning the corresponding one of the plurality of interchangeably removable data devices within the at least one opening; and, an Internet website for downloading audio data to the data device for playback by the phallic device, the Internet website configured to allow a user to make a customized recording for downloading to the data device.

2. A system for sexual stimulation comprising:

a phallic device comprising: a housing, at least one end cap attached to the housing, the at least one end cap including at least one opening for removably receiving a corresponding one of a plurality of interchangeably removable data devices, a data access device for accessing audio data from the interchangeably removable data device within the at least one opening, and, a sound emitter for emitting audio corresponding to the audio data accessed by the data access device from the data device, and the audio is playable by selectively positioning the corresponding one of the plurality of interchangeably removable data devices within the at least one opening; and, a remote device for recording audio data to the data device for playback by the phallic device, the remote device configured to record a user's voice and write audio data corresponding to the recorded voice to the data device.

3. A method of using a phallic device having an end cap, the end cap including at least one opening for removably receiving a corresponding one of a plurality of interchangeably removable data devices, a data access device for accessing audio data from the interchangeably removable data device within the opening, and, a sound emitter for emitting audio corresponding to the audio data accessed by the data access device from the data device, the method comprising:

customizing the audio data for playback by the phallic device by selectively downloading audio data from an Internet website to at least one of the interchangeably removable data devices;

selecting from amongst the plurality of interchangeably removable data devices; and positioning the selected interchangeably removable data device within the at least one opening to thereby allow the data access device to access the audio data thereon.

4. A method of using a phallic device having an end cap, the end cap including at least one opening for removably receiving a corresponding one of a plurality of interchangeably removable data devices, a data access device for accessing audio data from the interchangeably removable data device within the opening, and, a sound emitter for emitting audio corresponding to the audio data accessed by the data access device from the data device, the method comprising:

customizing the audio data for playback by the phallic device by selecting from amongst the plurality of interchangeably removable data devices, inserting the removed data device into a data device slot of a network device, and selectively downloading audio data from the network device to the removed data device; and positioning the selected interchangeably removable data device within the at least one opening to thereby allow the data access device to access the audio data thereon.

5. A method of using a phallic device having an end cap, the end cap including at least one opening for removably receiving a corresponding one of a plurality of interchangeably removable data devices, a data access device for accessing audio data from the interchangeably removable data device within the opening, and, a sound emitter for emitting audio corresponding to the audio data accessed by the data access device from the data device, the method comprising:

customizing the audio data for playback by the phallic device by recording a user's voice and writing audio data corresponding to the recorded voice to at least one of the interchangeably removable data devices;

selecting from amongst the plurality of interchangeably removable data devices; and, positioning the selected interchangeably removable data device within the at least one opening to thereby allow the data access device to access the audio data thereon.

* * * * *